(12) United States Patent  (10) Patent No.: US 7,582,791 B2
Araki et al.  (45) Date of Patent: Sep. 1, 2009

(54) PROCESS FOR PRODUCING OPTICALLY ACTIVE ESTER

(75) Inventors: Takaaki Araki, Higashimurayama (JP); Yukiyoshi Yamazaki, Higashimurayama (JP); Kimiyuki Shibuya, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 12/063,440

(22) PCT Filed: Aug. 24, 2006

(86) PCT No.: PCT/JP2006/316624
§ 371 (c)(1),
(2), (4) Date: Feb. 11, 2008

(87) PCT Pub. No.: WO2007/023906
PCT Pub. Date: Mar. 1, 2007

(65) Prior Publication Data
US 2009/0118535 A1 May 7, 2009

(30) Foreign Application Priority Data
Aug. 25, 2005 (JP) ............................. 2005-244641

(51) Int. Cl.
C07C 69/66 (2006.01)
(52) U.S. Cl. ........................ 560/179; 560/188
(58) Field of Classification Search ........................ None
See application file for complete search history.

(56) References Cited

FOREIGN PATENT DOCUMENTS

JP 4 36195 2/1992

OTHER PUBLICATIONS

Boudou et al, Advanced Synthesis & Catalysis, Chiral Scandium-Catalyzed Enantioselective Ring-Opening of meso-Epoxides with N-Heterocycle, Alcohol and Thiol Derivatives in Water, 2006, 348(18), pp. 2585-2589.*

Juan Riego, et al., "Regioselective ALPO$_4$-AL$_2$O$_3$ Promoted Ring-Opening of 2,3-Epoxy Esters", Chemistry Letters, No. 9, pp. 1565-1568, 1986.

Varinder K. Aggarwal, et al., "Highly Enantioselective Darzens Reaction of a Camphor-Derived Sulfonium Amide to Give Glycidic Amides and Their Applications in Synthesis", J. Am. Chem. vol. 124, No. 34, pp. 9964-9965, 2002.

Suk-ku Kang, et al., "Highly Regioselective Nucleophilic Substitution of Cyclic Carbonates of threo-2,3-Dihydroxy Esters: Synthesis of Optically Pure Beta-Hydroxy Esters", J. Chem. Soc. Perkin Trans. I, No. 24, pp. 3513-3514, 1994.

* cited by examiner

*Primary Examiner*—Paul A Zucker
(74) *Attorney, Agent, or Firm*—Oblon, Spivak, McClelland, Maier & Neustadt, P.C.

(57) ABSTRACT

A process for producing an optically active 2-hydroxybutyric ester (1), characterized by including reacting an optically active 2,3-epoxybutyric ester (2) with a thiol in the presence of scandium trifluoromethanesulfonate or ytterbium trifluoromethanesulfonate, to thereby produce Compound (3), and subjecting Compound (3) to desulfurization reaction:

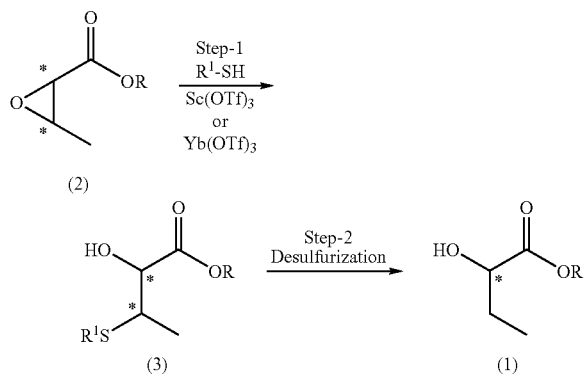

(wherein R represents a C1 to C6 alkyl group or a C7 or C8 aralkyl group; $R^1$ represents a C1 to C12 alkyl group or a phenyl group; and * represents S- or R-absolute configuration). The present invention provides a process for producing an optically active 2-hydroxybutyric ester at high yield and high optical purity.

3 Claims, No Drawings

PROCESS FOR PRODUCING OPTICALLY ACTIVE ESTER

TECHNICAL FIELD

The present invention relates to a process for producing an optically active 2-hydroxybutyric ester, which is a useful material for producing pharmaceuticals, pesticides, and industrial products.

BACKGROUND ART

Optically active 2-hydroxybutyric esters are compounds useful as a reagent or a starting material for producing pharmaceuticals, pesticides, and industrial products. For example, these esters serve as an important starting material for producing (R)-2-[3-[[N-(benzoxazol-2-yl)-N-3-(4-methoxyphenoxy)propyl]aminomethyl]phenoxy]butyric acid, which is a PPARα-selective activating agent and serves as a useful prophylactic and/or therapeutic agent for hyperlipemia, arteriosclerosis, diabetes, diabetes complications, inflammation, heart diseases, etc., and is represented by the following formula (A):

[F1]

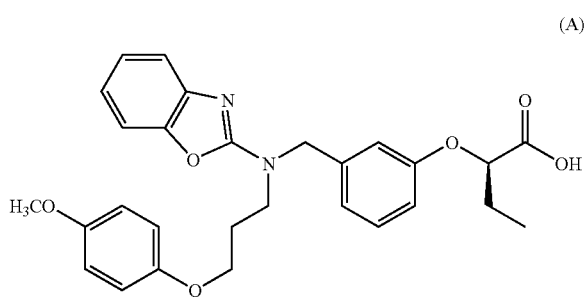

(A)

(Patent Document 1).

These optically active 2-hydroxybutyric esters are commercially available reagents (Aldrich), but are very expensive products. Hitherto, as shown in the following schemes, there have been known several processes for producing an optically active 2-hydroxycarboxylic ester derivative; for example, 1) a process for producing an optically active 2-hydroxybutyric ester through asymmetric reduction of a 2-ketobutyric ester by use of baker's yeast (Non-Patent Document 1); 2) a process for producing an optically active 2-hydroxybutyric ester from L-methionine as a starting material (Non-Patent Documents 2 and 3); 3) a process for producing an optically active 2-hydroxycarboxylic ester derivative through asymmetric reduction of an acrylic derivative (Non-Patent Document 4); 4) a process for producing an optically active 2-hydroxycarboxylic derivative from an aldehyde starting material via an optically active cyanohydrin form (Patent Document 2); and 5) a process for producing a 2-hydroxybutyric ester from a 2,3-epoxybutyric ester as a starting material via regio-selective epoxide-ring-opening reaction (Non-Patent Document 5).

[F2]

1)

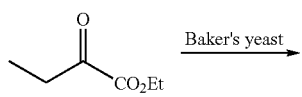

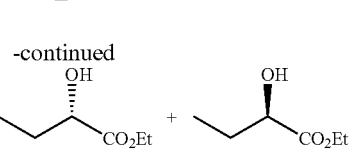

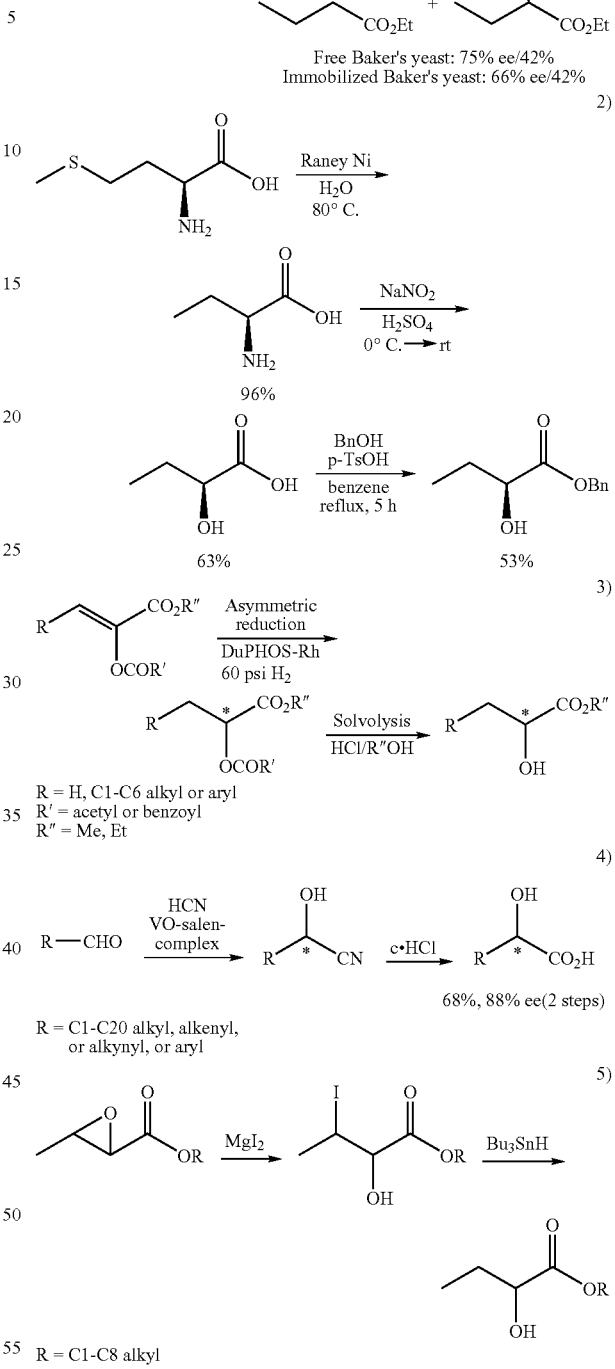

However, according to the process 1), chemical yield and optical purity (S-configuration) of the produced 2-hydroxybutyric ester are 42% and 75%, respectively (by use of free baker's yeast) and 42% and 66%, respectively (by use of immobilized baker's yeast). Thus, the process 1) is not suited for the production of high-optical purity 2-hydroxybutyric ester and is not considered an industrially applicable process. In addition, a 2-ketobutyric ester is chemically unstable (Non-Patent Document 1) and very expensive, which is problematic. The process 1) cannot be applied to production of an optically active 2-hydroxybutyric ester of R-configuration.

According to the process 2), a target optically active 2-hydroxybutyric ester can be produced from inexpensive L-methionine as a starting material. However, three steps are required for the target product, resulting in low overall yield, and a large amount of solvent is required for reaction and post treatment. Thus, the process 2) has problematically poor efficiency in terms of production conditions. In addition, since the process 2) includes a step of forming an unstable diazonium salt, reaction conditions are difficult to control, leading to variation in yield and optical purity of the target product. On a certain production scale, optical purity may drop considerably.

According to the process 3), the double bond of a 2-acyloxyacrylic ester derivative is asymmetrically reduced in the presence of an asymmetric catalyst, followed by solvolysis with an acid, whereby a target compound can be produced in high optical purity. However, the 2-acyloxyacrylic ester derivative serving as a starting material is produced through a complicated step, and the process includes preparation of an expensive asymmetric ligand and performing asymmetric reduction under high hydrogen pressure. Thus, the process 3) is not considered an industrially advantageous process.

According to the process 4), a 2-hydroxycarboxylic derivative is produced through two steps including asymmetric transformation of an aldehyde to a cyanohydrin and subsequent hydrolysis. However, preparation of an asymmetric ligand of the catalyst requires a very complex. Depending on a substituent of a reaction substrate, optical purity and chemical yield of the target compound are prone to vary, which is one disadvantage of the process.

The process 5) includes two steps: regio-selectively opening the epoxy ring of an 2,3-epoxybutyric ester by magnesium iodide and, subsequently, performing deiodation reaction, to thereby produce a 2-hydroxybutyric ester. The process has problems including a drop in regio-selectivity of ring-opening reaction caused by undesired reaction temperature, water present in the reaction system, etc.; and unavoidable use of a tin reagent which is stoichiometrically toxic in the subsequent deiodation reaction. Thus, the process 5) is not considered a useful method.

Under such circumstances, demand has arisen for the development of a new process which realizes production of an optically active 2-hydroxybutyric ester in high yield and high optical purity.

Patent Document 1: WO2005/023777, pamphlet
Patent Document 2: Japanese Unexamined Patent Application Publication No. 2004-533490
Non-Patent Document 1: J. Org. Chem., 1988, 53, 2589-2593
Non-Patent Document 2: J. Org. Chem., 1986, 51, 1713-1719
Non-Patent Document 3: Chirality, 1996, 51, 225-233
Non-Patent Document 4: J. Am. Chem. Soc., 1998, 120, 4345-4353
Non-Patent Document 5: Tetrahedron Lett., 1987, 28, 4435-4436

DISCLOSURE OF THE INVENTION

Problems To Be Solved By The Invention

An object of the present invention is to provide a process for producing an optically active 2-hydroxybutyric ester in a highly good yield and considerably high optical purity under mild reaction conditions.

Means For Solving The Problems

As shown in the following reaction scheme:

[F3]

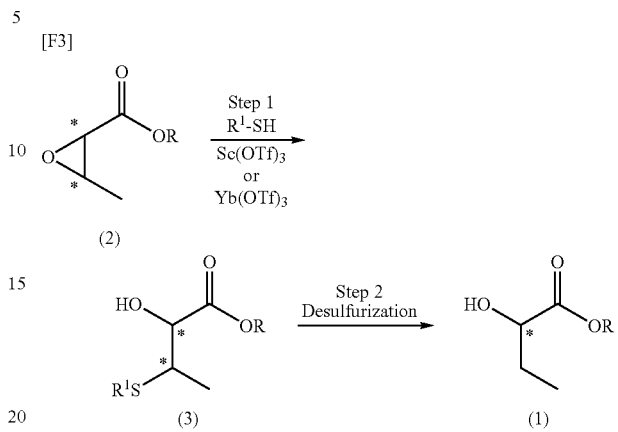

(wherein R represents a C1 to C6 alkyl group or a C7 or C8 aralkyl group; $R^1$ represents a C1 to C12 alkyl group or a phenyl group; and * represents S- or R-absolute configuration), the present inventors have employed an optically active 2,3-epoxybutyric ester (2), which can be supplied in a large amount at comparatively low cost through the enzymatic method, and have studied the effect of Lewis acids on reaction of the 2,3-epoxybutyric ester with a thiol. As a result, the inventors have found that use of scandium trifluoromethanesulfonate or ytterbium trifluoromethanesulfonate, which is a recoverable and recyclable Lewis acid, realizes high-yield production of Compound (3) via regio-selective opening of the epoxy ring (see the Examples hereinbelow), and that an optically active 2-hydroxybutyric ester (1) can be produced in high yield and high optical purity via subsequent desulfurization.

Accordingly, the present invention is directed to a process for producing an optically active 2-hydroxybutyric ester (1), characterized in that the process comprises reacting an optically active 2,3-epoxybutyric ester (2) with a thiol represented by $R^1$—SH in the presence of scandium trifluoromethanesulfonate or ytterbium trifluoromethanesulfonate, to thereby form Compound (3), and subjecting Compound (3) to desulfurization reaction.

The present invention is also directed to a process for producing Compound (3), characterized in that the process comprises reacting an optically active 2,3-epoxybutyric ester (2) with a thiol represented by $R^1$—SH in the presence of scandium trifluoromethanesulfonate or ytterbium trifluoromethanesulfonate.

Effects Of The Invention

According to the process of the present invention, an optically active 2-hydroxybutyric ester, which is a useful material for producing pharmaceuticals, pesticides, and industrial products, can be produced in high yield and high optical yield.

BEST MODES FOR CARRYING OUT THE INVENTION

The reaction steps included in the production process of the present invention will now be described.

1. Step 1

In Step 1, an optically active 2,3-epoxybutyric ester (2) is reacted with a thiol $R^1$—SH (wherein $R^1$ has the same meaning as defined above) in the presence of scandium trifluoromethanesulfonate or ytterbium trifluoromethanesulfonate, to thereby produce an optically active 3-alkylthio-2-hydroxybutyric ester or an optically active 2-hydroxy-3-phenylthiobutyric ester (Compound (3)).

R in the optically active 2,3-epoxybutyric ester (2) and Compound (3) represents a C1 to C6 alkyl group or a C7 or C8 aralkyl group. Examples of preferred alkyl groups include methyl, ethyl, n-propyl, isopropyl, n-butyl, isobutyl, and t-butyl, with n-butyl being more preferred. Examples of preferred aralkyl groups include benzyl and phenethyl.

In the thiol $R^1$—SH, $R^1$ represents a C1 to C12 alkyl group or a phenyl group. Examples of preferred alkyl groups include methyl, ethyl, n-propyl, isopropyl, n-butyl, isobutyl, t-butyl, and n-dodecyl.

The thiol is generally used in an amount of 1 to 1.5 mol against 1 mol of optically active 2,3-epoxybutyric ester (2), preferably 1 mol.

This reaction is performed by use of the thiol in the co-presence of scandium trifluoromethanesulfonate or ytterbium trifluoromethanesulfonate. Of the two compounds, scandium trifluoromethanesulfonate is preferably used.

Scandium trifluoromethanesulfonate or ytterbium trifluoromethanesulfonate is used in the present invention in an amount of 0.2 to 1.5 mol against 1 mol of optically active 2,3-epoxybutyric ester (2), preferably 0.5 to 1 mol.

The reaction may be performed in the presence or absence of solvent. Preferably, the reaction is performed in a solvent.

No particular limitation is imposed on the solvent employed in the reaction, and any solvent may be employed so long as it is not involved in the reaction. Examples of the solvent include ethers such as diethyl ether, tetrahydrofuran, 1,4- and 1,3-dioxane, t-butyl methyl ether, monoglyme, and diglyme; aromatic hydrocarbons such as benzene, toluene, xylene, mesitylene, chlorobenzene, and o-dichlorobenzene; aliphatic hydrocarbons such as n-hexane, cyclohexane, n-octane, and n-decane; halohydrocarbons such as methylene chloride, dichloroethane, chloroform, and carbon tetrachloride; and water. Of these, ethers such as diethyl ether, tetrahydrofuran, 1,4- and 1,3-dioxane, t-butyl methyl ether, monoglyme, and diglyme; halohydrocarbons such as methylene chloride, dichloroethane, chloroform, and carbon tetrachloride; and water are preferred, with methylene chloride and chloroform being particularly preferred. These solvents may be used singly or in combination. No particular limitation is imposed on the amount of solvent employed.

The reaction is generally performed at −80 to 50° C., preferably 0 to 30° C. Generally, the reaction time is preferably 1 to 12 hours, more preferably 5 to 10 hours.

Since the reaction can be performed in the aforementioned employable solvents, dry conditions are not particularly required.

After completion of reaction, the reaction mixture is extracted with water and an organic solvent such as methylene chloride, chloroform, ethyl acetate, diethyl ether, or toluene, preferably chloroform, whereby Compound (3) can be separated from scandium trifluoromethanesulfonate or ytterbium trifluoromethanesulfonate. In other words, scandium trifluoromethanesulfonate or ytterbium trifluoromethanesulfonate can be completely recovered from the aqueous layer and reused, although most Lewis acids cannot be reused due to deterioration such as decomposition.

The optically active 2,3-epoxybutyric ester (2) is a known compound and may be produced through a known process (see, for example, JP-A-5-276966).

There has been reported the preparation of ethyl 2-hydroxy-3-phenylthiobutyrate by reaction of an epoxy compound with a thiol (Chem. Lett., 1986, 1565-1568). In the reported process, thiophenol is regioselectively reacted with ethyl 2,3-epoxybutyrate in the presence of aluminum phosphate-dialuminum trioxide. However, this process requires dry conditions and a comparatively long reaction period, and affords a low chemical yield (70%). In addition, a solvent is required in a 100-fold amount (V/W) or more against ethyl 2,3-epoxybutyrate as a starting material, which leads reaction operations, post-treatments, handling of inorganic reagents, etc. Thus, this process is not considered to be practical. In contrast, the process of the present invention realizes production of Compound (3) in an excellent yield under mild reaction conditions (see Comparative Example hereinbelow).

2. Step 2

In Step 2, Compound (3) is desulfurized, to thereby produce an optically active 2-hydroxybutyric ester (1).

R in formula (1) has the same meaning as defined above.

In Step 2, desulfurization may be performed via chemical reaction such as hydrogenolysis by use of Raney nickel, nickel boride ($Ni_2B$), or a similar substance; reductive hydrogenation by use of alkali metal/lower amine such as lithium/ethylamine; or reductive hydrogenation by use of zinc-mercury/hydrochloric acid. Among these reactions, hydrogenolysis by use of Raney nickel is preferred. In addition to Raney nickel, Celite may also be added to the reaction system.

In hydrogenolysis reaction by use of Raney nickel, Raney nickel is used in an amount of 0.5-fold to 15-fold (W/W) against Compound (3), preferably 2-fold to 12-fold (W/W), more preferably 5-fold to 10-fold (W/W).

When Raney nickel and Celite are used in combination, Celite is used in an amount of 0.1-fold to 5-fold (W/W) against Raney nickel, preferably 0.5-fold to 1.5-fold (W/W).

The reaction in Step 2 is performed in a solvent. Examples of the solvent include alcohols such as methanol, ethanol, and propanol; ethers such as diethyl ether, tetrahydrofuran, 1,4- and 1,3-dioxane, t-butyl methyl ether, monoglyme, and diglyme; ketones such as acetone and methyl ethyl ketone; aromatic hydrocarbons such as benzene, toluene, xylene, mesitylene, chlorobenzene, and o-dichlorobenzene; and water. Of these, alcohols such as methanol, ethanol, and propanol; and water are preferred. These solvents may be used singly or in combination. No particular limitation is imposed on the amount of solvent employed.

The reaction is generally performed at 30 to 100° C., preferably 50 to 80° C. Generally, the reaction time is preferably 1 to 12 hours, more preferably 5 to 10 hours.

In hydrogenolysis reaction by use of nickel boride, nickel boride is prepared upon use from nickel chloride ($NiCl_2$) and sodium borohydride ($NaBH_4$). Nickel chloride is used in an amount of 0.5 to 20 mol-eq. against Compound (3), preferably 1 to 15 mol-eq., more preferably 2 to 10 mol-eq. Sodium borohydride is used in an amount of 1 to 40 mol-eq. against Compound (3), preferably 5 to 35 mol-eq., more preferably 6 to 30 mol-eq. The solvent employed in the reaction is preferably ethanol, methanol, tetrahydrofuran, or water. The reaction temperature is generally 25 to 100° C., and the reaction time is generally 7 to 12 hours.

In reductive hydrogenation by use of lithium/ethylamine, ethylamine is preferably used in an amount of 50-fold to 100-fold (V/W) against Compound (3), and lithium is preferably used in an amount of 0.5-fold to 1.5-fold (W/W) against Compound (3). This reaction is performed in the absence of solvent. The reaction temperature is generally −78° C. to −20° C., and the reaction time is generally 1 to 5 hours.

In reductive hydrogenation by use of zinc-mercury/hydrochloric acid, zinc-mercury is preferably used in an amount of 10-fold to 50-fold (W/W) against Compound (3). Hydrochloric acid is preferably used in an amount of 2-fold to 5-fold (V/W). The solvent employed in the reaction is preferably ethanol. The reaction temperature is generally 25 to 80° C., and the reaction time is generally 1 to 10 hours.

In the present invention, if required, a target product of each reaction may be isolated through any purification method generally employed in organic synthetic chemistry; e.g., filtration, washing, drying, recrystallization, chromatographic processes, or distillation.

EXAMPLES

The present invention will next be described in more detail in the following examples.

Example 1

Synthesis of n-butyl(S)-2-hydroxy-(S)-3-phenylthiobutyrate

Scandium trifluoromethanesulfonate [Sc(OTf)$_3$] (311 mg) and thiophenol (0.064 mL) were sequentially added at room temperature to a solution of n-butyl (2S,3R)-2,3-epoxybutyrate (100 mg, 97.3% ee) (product of Osaka Organic Chemical Industry, Ltd.) in methylene chloride (5.0 mL), and the mixture was stirred at the same temperature for 10 hours. The reaction mixture was added to water (20 mL), and extracted with chloroform (20 mL×3). The organic layers were combined, and the combined organic layer was dried over sodium sulfate anhydrate and concentrated under reduced pressure. The residue was purified through silica gel column chromatography (n-hexane/ethyl acetate=5/1), to thereby yield colorless oil (117 mg, 95.3%).

IR(ATR); 3484, 2961, 2933, 2873, 1732, 1645, 1474, 1439, 1380, 1240, 1211, 1129, 1090, 1051, 1024, 951, 747, 692 cm$^{-1}$.

$^1$H-NMR(400 MHz, CDCl$_3$) δ; 0.94 (t, J=7 Hz, 3H), 1.27 (d, J=7 Hz, 3H), 1.38 (sext, J=7 Hz, 2H), 1.65 (quint, J=7 Hz, 2H), 3.01 (d, J=5 Hz, 1H), 3.65 (dq, J=7, 3 Hz, 1H), 4.14-4.25 (m, 2H), 4.29 (dd, J=5, 3 Hz, 1H), 7.25-7.34 (m, 3H), 7.48 (d, J=7 Hz, 2H).

EI-MS m/z; 268 (M$^+$)

Elemental analysis (as C$_{14}$H$_{20}$O$_3$S) calc.: C, 62.66; H, 7.51; S, 11.95. Found: C, 62.66; H, 7.61; S, 11.70.

Example 2

Synthesis of n-butyl(S)-2-hydroxy-(S)-3-phenylthiobutyrate

Ytterbium trifluoromethanesulfonate [Yb(OTf)$_3$] (196 mg) and thiophenol (0.032 mL) were sequentially added at room temperature to a solution of n-butyl (2S,3R)-2,3-epoxybutyrate (50 mg) in methylene chloride (3.0 mL), and the mixture was stirred at the same temperature for 24 hours. The reaction mixture was added to water (20 mL), and extracted with chloroform (20 mL×3). The organic layers were combined, and the combined organic layer was dried over sodium sulfate anhydrate and concentrated under reduced pressure. The residue was purified through preparative thin-layer chromatography (n-hexane/ethyl acetate=5/1), to thereby yield colorless oil (69 mg, 81.3%).

Example 3

Synthesis of n-butyl(S)-2-hydroxy-(S)-3-ethylthiobutyrate

Scandium trifluoromethanesulfonate [Sc(OTf)$_3$] (311 mg) and ethanethiol (0.047 mL) were sequentially added at room temperature to a solution of n-butyl (2S,3R)-2,3-epoxybutyrate (100 mg) in methylene chloride (5.0 mL), and the mixture was stirred at the same temperature for 7 hours. The reaction mixture was added to water (20 mL), and extracted with chloroform (20 mL×3). The organic layers were combined, and the combined organic layer was dried over anhydrous sodium sulfate and concentrated under reduced pressure. The residue was purified through silica gel column chromatography (n-hexane/ethyl acetate=5/1), to thereby yield colorless oil (116 mg, 83.4%).

IR(ATR); 3490, 2962, 2931, 2873, 1732, 1456, 1379, 1260, 1239, 1209, 1130, 1088, 1060, 980, 784, 766, 738, 699 cm$^{-1}$.

$^1$H-NMR (400 MHz, CDCl$_3$) δ; 0.95 (t, J=7 Hz, 3H), 1.24 (d, J=7 Hz, 3H), 1.28 (t, J=7 Hz, 3H), 1.40 (sext, J=7 Hz, 2H), 1.63-1.70 (m, 2H), 2.57-2.71 (m, 2H), 3.03 (d, J=5 Hz, 1H), 3.20 (dq, J=7, 3 Hz, 1H), 4.17-4.27 (m, 2H), 4.33 (dd, J=5, 3 Hz, 1H).

EI-MS m/z; 220 (M$^+$)

Example 4

Synthesis of n-butyl(S)-2-hydroxy-(S)-3-dodecylthiobutyrate

Scandium trifluoromethanesulfonate [Sc(OTf)$_3$] (156 mg) and 1-dodecanethiol (0.076 mL) were sequentially added at room temperature to a solution of n-butyl (2S,3R)-2,3-epoxybutyrate (50 mg) in methylene chloride (4.0 mL), and the mixture was stirred at the same temperature for 10 hours. The reaction mixture was added to water (20 mL), and extracted with chloroform (20 mL×3). The organic layers were combined, and the combined organic layer was dried over anhydrous sodium sulfate and concentrated under reduced pressure. The residue was purified through silica gel column chromatography (n-hexane/ethyl acetate=5/1), to thereby yield colorless oil (97 mg, 84.9%).

IR(ATR); 3471, 2958, 2924, 2854, 1733, 1458, 1379, 1210, 1129, 1058, 1020, 983, 965, 837, 807, 777, 738, 687 cm$^{-1}$.

$^1$H-NMR (400 MHz, CDCl$_3$) δ; 0.88 (t, J=7 Hz, 3H), 0.95 (t, J=7 Hz, 3H), 1.23-1.45 (m, 23H), 1.59 (quint, J=7 Hz, 2H), 1.67 (quint, J=7 Hz, 2H), 2.54-2.66 (m, 2H), 3.03 (d, J=5 Hz, 1H), 3.17 (dq, J=7, 3 Hz, 1H), 4.16-4.27 (m, 2H), 4.32 (dd, J=5, 3 Hz, 1H).

EI-MS m/z; 360 (M$^+$)

Example 5

Synthesis of n-butyl(S)-2-hydroxybutyrate n-Butyl(S)-2-hydroxy-(S)-3-phenylthiobutyrate (60 mg) was dissolved in ethanol (2.0 mL). Celite (240 mg) and an ethanol solution (3.0 mL) of Raney nickel (360 mg) were sequentially added at room temperature to the solution, and the mixture was stirred at 80° C. for 10 hours. The reaction mixture was filtered through Celite, and the filtrate was added to water (20 mL), followed by extraction with diethyl ether (20 mL×3). The organic layers were combined, and the combined organic layer was dried over anhydrous sodium sulfate and concentrated under reduced pressure. The residue was purified through silica gel column chromatography (methylene chloride), to thereby yield colorless oil (36 mg, 100%).

IR(ATR); 3483, 2962, 2935, 2876, 1731, 1463, 1381, 1244, 1206, 1132, 1059, 994, 841, 738, 678 cm$^{-1}$.

$^1$H-NMR (400 MHz, CDCl$_3$) δ; 0.93 (t, J=7.8 Hz, 3H), 0.94 (t, J=7.8 Hz, 3H), 1.37 (qt, J=7.5, 7.4 Hz, 2H), 1.59-1.72 (m, 3H), 1.77-1.85 (m, 1H), 2.71 (d, J=5.6 Hz, 1H), 4.11-4.23 (m, 3H).

b.p.; 66-68° C. (2 mmHg)

EI-MS m/z; 161 (M$^+$+H).

Elemental analysis (as C$_8$H$_{16}$O$_3$) calc.: C, 59.97; H, 10.07. Found: C, 60.03; H, 10.09.

Optical Purity:

As shown in the following scheme, optical purity was determined through HPLC analysis with derivatization to a 4-nirtobenzoic ester.

[F4]

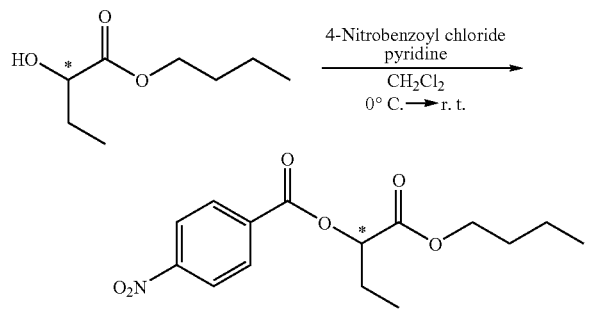

n-Butyl(S)-2-hydroxybutyrate (30 mg) was dissolved in a mixture of methylene chloride (1 mL) and pyridine (0.02 mL). 4-Nitrobenzoyl chloride (35 mg) was added at 0° C. to the mixture, followed by stirring at 0° C. for 10 minutes and at room temperature for 5 hours. Water (5 mL) was added to the reaction mixture with stirring for 5 minutes, and chloroform (5 mL) was added thereto. The organic layer was washed sequentially with 4M hydrochloric acid, water, aqueous saturated sodium hydrogencarbonate solution, and saturated brine. The organic layer was dried over sodium sulfate anhydrate and concentrated under reduced pressure. The residue was purified through collective thin-layer chromatography (n-hexane/chloroform=1/1), to thereby yield 31 mg of colorless oil (54%, optical purity: 97.2% ee).

Measurement Conditions (HPLC)

Column: CHIRALPAK AD

Column temperature: 35° C.

Solvent: n-hexane/ethanol=60/40

Flow rate: 1 mL/min

Retention time: 5.96 min (R form: 4.43 min)

Comparative Example 1

Compound (2a) shown hereinbelow was reacted with a thiol (ethanethiol, dodecanethiol, or thiophenol) in the presence of a Lewis acid selected from a variety of species, to thereby produce Compounds (3a) (Step 1). The results are shown in Tables 1 and 2.

TABLE 1

| No. | R$^{1a}$ | Lewis acid | Solvent | Reaction time | Results |
|---|---|---|---|---|---|
| 1 | Et | ZnCl$_2$ | CH$_2$Cl$_2$ | 20 hr | Cl form (main product) |
| 2 | Et | ZrCl$_4$ | CH$_2$Cl$_2$ | 20 hr | Cl form (main product) |
| 3 | Et | AlCl$_3$ | CH$_2$Cl$_2$ | 3 hr | Cl form (main product) |
| 4 | Et | AlEt$_2$Cl | CH$_2$Cl$_2$ | 3 hr | Mixture |
| 5 | Et | VCl$_3$ | CH$_2$Cl$_2$ | 20 hr | Cl form + 2a |
| 6 | Et | LiClO$_4$ | CH$_2$Cl$_2$ | 20 hr | Reaction did not proceed |
| 7 | Et | ZnCl$_2$ | THF | 20 hr | Cl form + 2a |
| 8 | Et | ZrCl$_4$ | THF | 20 hr | Mixture containing starting materials |
| 9 | Et | AlCl$_3$ | THF | 20 hr | Mixture |
| 10 | Et | AlEt$_2$Cl | THF | 20 hr | Mixture containing starting materials |
| 11 | Et | VCl$_3$ | THF | 20 hr | Reaction did not proceed |
| 12 | Et | LiClO$_4$ | THF | 20 hr | Reaction did not proceed |
| 13 | Et | Sc(OTf)$_3$ (1.0 eq) | CH$_2$Cl$_2$ | 7 hr | 3a: 83.4%, 4a: 0% |
| 14 | C$_{12}$H$_{25}$ | Sc(OTf)$_3$ (1.0 eq) | CH$_2$Cl$_2$ | 10 hr | 3a: 84.9%, 4a: 0% |

C1 form:

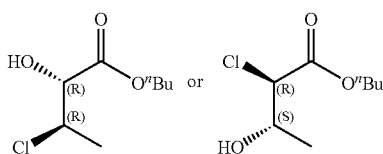

TABLE 2

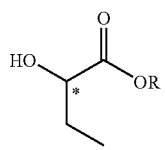

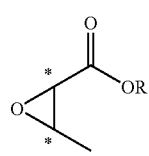

| No. | Lewis acid | Reaction time | Results |
| --- | --- | --- | --- |
| 1 | $Zn(OTf)_2$ | 24 hr | Reaction did not proceed |
| 2 | $Ti(O^iPr)_4$ | 24 hr | Reaction did not proceed |
| 3 | $Al(OTf)_3$ | 12 hr | Mixture |
| 4 | $Al_2O_3$ | 24 hr | 3a: trace amount, 4a: 19.2% |
| 5 | $BF_3 \cdot Et_2O$ | 8 hr | 3a: 33.7%, 4a: trace amount |
| 6 | $La(OTf)_3$ | 24 hr | 3a: 23.7%, 4a: trace amount |
| 7 | $Yb(OTf)_3$ | 24 hr | 3a: 81.3%, 4a: 0% |
| 8 | $Sc(OTf)_3$ | 10 hr | 3a: 95.3%, 4a: 0% |

As shown in Tables 1 and 2 evidently, target Compounds (3a) can be produced in high yield only in the cases employing scandium trifluoromethanesulfonate or ytterbium trifluoromethanesulfonate as a Lewis acid. Therefore, the process of the present invention has been proven to be a remarkably excellent process.

The invention claimed is:

1. A process for producing an optically active 2-hydroxybutyric ester represented by formula (1):

[F3]

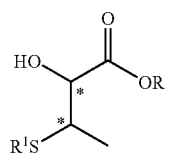
(1)

(wherein R represents a C1 to C6 alkyl group or a C7 or C8 aralkyl group, and * represents S- or R-absolute configuration), characterized in that the process comprises
reacting an optically active 2,3-epoxybutyric ester represented by formula (2):

[F1]

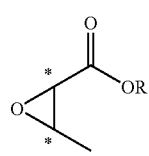
(2)

(wherein R and * have the same meanings as defined above) with a thiol represented by $R^1$—SH (wherein $R^1$ represents a C1 to C12 alkyl group or a phenyl group) in the presence of scandium trifluoromethanesulfonate or ytterbium trifluoromethanesulfonate, to thereby produce a compound represented by formula (3):

[F2]

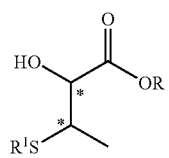
(3)

(wherein R, $R^1$, and * have the same meanings as defined above), and
subjecting the compound represented by formula (3) to desulfurization reaction.

2. A process as described in claim 1, wherein the desulfurization reaction is hydrogenolysis by use of Raney nickel.

3. A process for producing a compound represented by formula (3):

[F5]

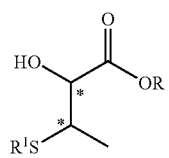
(3)

(wherein R represents a C1 to C6 alkyl group or a C7 or C8 aralkyl group; $R^1$ represents a C1 to C12 alkyl group or a phenyl group; and * represents S- or R-absolute configuration), characterized in that the process comprises
reacting an optically active 2,3-epoxybutyric ester represented by formula (2):

[F4]

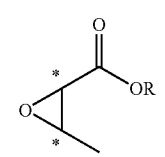
(2)

(wherein R and * have the same meanings as defined above) with a thiol represented by $R^1$—SH (wherein $R^1$ has the same meaning as defined above) in the presence of scandium trifluoromethanesulfonate or ytterbium trifluoromethanesulfonate.

* * * * *